(12) United States Patent
Pacetti et al.

(10) Patent No.: US 8,430,923 B2
(45) Date of Patent: Apr. 30, 2013

(54) RADIOPAQUE INTRALUMINAL STENT

(75) Inventors: Stephen Pacetti, San Jose, CA (US); Pamela A. Kramer, San Jose, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 985 days.

(21) Appl. No.: 11/736,979

(22) Filed: Apr. 18, 2007

(65) Prior Publication Data
US 2007/0185564 A1 Aug. 9, 2007

Related U.S. Application Data

(62) Division of application No. 09/534,071, filed on Mar. 24, 2000, now Pat. No. 7,250,058.

(51) Int. Cl.
*A61F 2/06* (2006.01)
*A61M 29/00* (2006.01)

(52) U.S. Cl.
USPC .......................... 623/1.15; 606/108; 606/198

(58) Field of Classification Search .......... 623/1.1–1.22; 606/191–198
See application file for complete search history.

(56) References Cited

U.S. PATENT DOCUMENTS

| | | | |
|---|---|---|---|
| 4,685,977 A * | 8/1987 | Chang | 148/556 |
| 5,061,275 A | 10/1991 | Wallsten et al. | |
| 5,330,826 A | 7/1994 | Taylor et al. | |
| 5,421,955 A | 6/1995 | Lau et al. | |
| 5,514,154 A | 5/1996 | Lau et al. | |
| 5,569,295 A | 10/1996 | Lam | |
| 5,603,721 A | 2/1997 | Lau et al. | |
| 5,618,299 A | 4/1997 | Khosravi et al. | |
| 5,628,787 A | 5/1997 | Mayer | |
| 5,630,840 A | 5/1997 | Mayer | |
| 5,636,641 A | 6/1997 | Fariabi | |
| 5,649,952 A | 7/1997 | Lam | |
| 5,725,572 A | 3/1998 | Lam et al. | |
| 5,728,158 A | 3/1998 | Lau et al. | |
| 5,735,893 A | 4/1998 | Lau et al. | |
| 5,759,192 A | 6/1998 | Saunders | |
| 5,766,238 A | 6/1998 | Lau et al. | |
| 5,824,077 A | 10/1998 | Mayer | |
| 5,849,037 A | 12/1998 | Frid | |
| 5,876,432 A | 3/1999 | Lau et al. | |
| 5,891,191 A | 4/1999 | Stinson | |

(Continued)

FOREIGN PATENT DOCUMENTS

| EP | 0804934 | 3/1997 |
|---|---|---|
| WO | WO 97/33534 | 9/1997 |

(Continued)

OTHER PUBLICATIONS

Giessen et al. "Coronary Stenting with a New Radiopaque Balloon Expandable Endoprosthesis in Pigs" Presented in part at the 62nd Annual Scientific Sessions of the American Heart Association, Nov. 13-16, 1989, New Orleans, LA.

(Continued)

*Primary Examiner* — Vy Q Bui
(74) *Attorney, Agent, or Firm* — Workman Nydegger; Jonathan D. Feuchtwang (57) ABSTRACT

The present invention includes a radiopaque stent comprising a cylindrical main body. The tubular main body comprises a cobalt chromium alloy that comprises cobalt, chromium and one or more radiopaque materials.

18 Claims, 6 Drawing Sheets

U.S. PATENT DOCUMENTS

| | | | |
|---|---|---|---|
| 5,984,973 A * | 11/1999 | Girard et al. | 623/2.38 |
| 6,027,528 A | 2/2000 | Tomonto et al. | |
| 6,287,331 B1 * | 9/2001 | Heath | 623/1.15 |
| 6,419,693 B1 * | 7/2002 | Fariabi | 623/1.18 |
| 6,620,192 B1 * | 9/2003 | Jalisi | 623/1.15 |
| 7,105,018 B1 | 9/2006 | Yip et al. | |
| 7,156,869 B1 | 1/2007 | Pacetti | |
| 7,250,058 B1 | 7/2007 | Pacetti et al. | |
| 7,413,574 B2 | 8/2008 | Yip et al. | |
| 2002/0032477 A1 | 3/2002 | Helmus et al. | |
| 2005/0059889 A1 | 3/2005 | Mayer | |
| 2005/0060025 A1 | 3/2005 | Mackiewicz et al. | |
| 2006/0190070 A1 | 8/2006 | Dieck et al. | |
| 2006/0259126 A1 | 11/2006 | Lenz | |
| 2006/0271169 A1 | 11/2006 | Lye et al. | |
| 2006/0287709 A1 | 12/2006 | Rao | |
| 2007/0135891 A1 | 6/2007 | Schneider | |
| 2007/0173925 A1 | 7/2007 | Fliedner | |
| 2007/0185564 A1 | 8/2007 | Pacetti et al. | |
| 2007/0219624 A1 | 9/2007 | Brown et al. | |
| 2007/0265699 A1 | 11/2007 | Grewe et al. | |
| 2007/0270942 A1 | 11/2007 | Thomas | |
| 2008/0160259 A1 | 7/2008 | Nielson et al. | |
| 2008/0177371 A1 | 7/2008 | Ryan et al. | |
| 2008/0183280 A1 | 7/2008 | Agnew et al. | |
| 2008/0208308 A1 | 8/2008 | Allen et al. | |
| 2008/0208352 A1 | 8/2008 | Krivoruchko et al. | |
| 2008/0215132 A1 | 9/2008 | Ryan et al. | |
| 2008/0262600 A1 | 10/2008 | Jalisi | |
| 2009/0030500 A1 | 1/2009 | Weber | |
| 2009/0048659 A1 | 2/2009 | Weber et al. | |
| 2009/0093871 A1 | 4/2009 | Rea et al. | |
| 2009/0118822 A1 | 5/2009 | Holman et al. | |
| 2009/0149947 A1 | 6/2009 | Frohwitter | |
| 2009/0240324 A1 | 9/2009 | Smith | |
| 2009/0258050 A1 | 10/2009 | Lindsay et al. | |
| 2009/0259299 A1 | 10/2009 | Moloney | |
| 2009/0276033 A1 | 11/2009 | Mayer | |
| 2010/0004733 A1 | 1/2010 | Atanasoska et al. | |
| 2010/0217373 A1 | 8/2010 | Boyle et al. | |
| 2010/0222873 A1 | 9/2010 | Atanasoska et al. | |
| 2010/0241210 A1 | 9/2010 | Patadia | |

FOREIGN PATENT DOCUMENTS

| | | |
|---|---|---|
| WO | WO 99/15108 | 4/1999 |
| WO | WO 00/54704 | 9/2000 |
| WO | WO 01/15632 | 3/2001 |
| WO | WO 01/17577 | 3/2001 |
| WO | WO 01/72349 | 4/2001 |
| WO | WO 02/078763 | 10/2002 |

OTHER PUBLICATIONS

Cordis Palmaz Blue .018 Peripheral Stent System http://www.jjnordic.com/Lists/FileList1/Attatchments/174/PalmazBlue_018_Brochure.PDF.
U.S. Appl. No. 09/534,071, Mail Date Sep. 17, 2002, Office Action.
U.S. Appl. No. 09/534,071, Mail Date Dec. 18, 2002, Office Action.
U.S. Appl. No. 09/534,071, Mail Date Jul. 9, 2003, Office Action.
U.S. Appl. No. 09/534,071, Mail Date Aug. 29, 2005, Office Action.
U.S. Appl. No. 09/534,071, Mail Date Nov. 15, 2005, Office Action.
U.S. Appl. No. 09/534,071, Mail Date Mar. 13, 2006, Office Action.
U.S. Appl. No. 09/534,071, Mail Date Sep. 13, 2006, Office Action.
U.S. Appl. No. 09/534,071, Mail Date Feb. 12, 2007, Notice of Allowance.
U.S. Appl. No. 09/534,071, Mail Date Jul. 11, 2007, Issue Notification.
U.S. Appl. No. 13/618,602, mailed Mar. 4, 2013.

* cited by examiner

RADIOPAQUE INTRALUMINAL STENT

This application is a divisional of U.S. application Ser. No. 09/534,071, filed Mar. 24, 2000.

BACKGROUND OF THE INVENTION

The present invention relates to a radiopaque intraluminal stent comprised of a cobalt chromium alloy with one or more radiopaque elements and to a method for making the radiopaque intraluminal stent.

Intraluminal stents implanted with percutaneous methods have become a standard adjunct to procedures such as balloon angioplasty in the treatment of atherosclerotic disease of the arterial system. Stents, by preventing acute vessel recoil, improve long term patient outcome and have other benefits such as securing vessel dissections.

Intraluminal stents comprise generally tubular-shaped devices which are constructed to hold open a segment of a blood vessel or other anatomical lumen. Intraluminal stents are used in treatment of diseases such as atherosclerotic stenosis as well as diseases of the stomach and esophagus, and for urinary tract applications. Adequate stent function requires a precise placement of the stent over a lesion or site of plaque or other lumen site in need of treatment. Typically, the stent is delivered to a treatment site by a delivery catheter that comprises an expandable portion for expanding the stent within the lumen.

One delivery catheter onto which the stent is mounted is a balloon delivery catheter similar to those used for balloon angioplasty procedures. In order for the stent to remain in place on the balloon during delivery to the site of damage within a lumen, the stent is compressed onto the balloon. The catheter and stent assembly is introduced within a patient's vasculature using a guiding catheter. The guidewire is disposed across the damaged arterial section and then the catheter-stent assembly is advanced over the guidewire within the artery until the stent is directly within the lesion or the damaged section.

The balloon of the catheter is expanded, expanding the stent against the artery. The artery is preferably slightly expanded by the expansion of the stent to seat or otherwise fix the stent to prevent movement. In some circumstances during treatment of stenotic portions of the artery, the artery may have to be expanded considerably in order to facilitate passage of blood or other fluid therethrough. In the case of a self expanding stent, the stent is expanded by retraction of a sheath or actuation of release mechanism. Self expanding stents appose themselves to the vessel wall automatically and require a dilatation balloon only for post dilatation.

These manipulations are performed within the body of a patient by an interventionalist who relies upon both placement markers on the stent catheter and on the radiopacity of the stent itself. The stent radiopacity arises from a combination of stent material and stent pattern. After deployment within the vessel, the stent radiopacity should allow adequate visibility of both the stent and the underlying vessel and/or lesion morphology under fluoroscopic visualization.

Other conventional stents incorporate materials, such as tantalum, that aid in identifying the location of the stent within a vessel but illuminate so brightly under fluoroscopy that the underlying vessel morphology is obscured, thereby impairing the ability of the interventionalist to repair the lesion. Other stents incorporate radiopaque markers that facilitate stent location, but do not allow adequate stent visualization to assist determination of optimal deployment.

SUMMARY OF THE INVENTION

One embodiment of the present invention includes a radiopaque stent. The radiopaque stent comprises a cylindrical main body. The cylindrical main body comprises a cobalt chromium alloy that comprises cobalt, chromium and one or more radiopaque materials.

Another embodiment of the present invention includes an assembly comprising a catheter and a radiopaque stent. The radiopaque stent comprises a cobalt chromium alloy that comprises cobalt, chromium and one or more radiopaque materials.

One other embodiment of the present invention includes a method for making a radiopaque stent. The method comprises providing a tube. The tube comprises a cobalt chromium alloy. The alloy comprises cobalt, chromium and one or more radiopaque materials. The tube is shaped to form a radiopaque stent.

Another embodiment of the present invention includes a method for positioning a stent in a lumen of a living being. The method comprises providing a radiopaque stent. The radiopaque stent comprises a cylindrical main body that comprises a cobalt chromium alloy. The cobalt chromium alloy comprises cobalt, chromium, and one or more radiopaque materials, deformable in a ductile manner, rendering the radiopaque stent balloon expandable on the delivery system. The stent is unexpanded. The stent is transported to a lesion site in the lumen wherein the stent is optionally imaged during transport. The stent is expanded to contact the lesion. The radiopaque stent is imaged during or after expanding the stent.

Another embodiment of the present invention includes a radiopaque stent comprising one or more wires. The wires comprise a cobalt chromium alloy. The cobalt chromium alloy comprises cobalt, chromium and one or more radiopaque materials.

DETAILED DESCRIPTION

Figure 1:
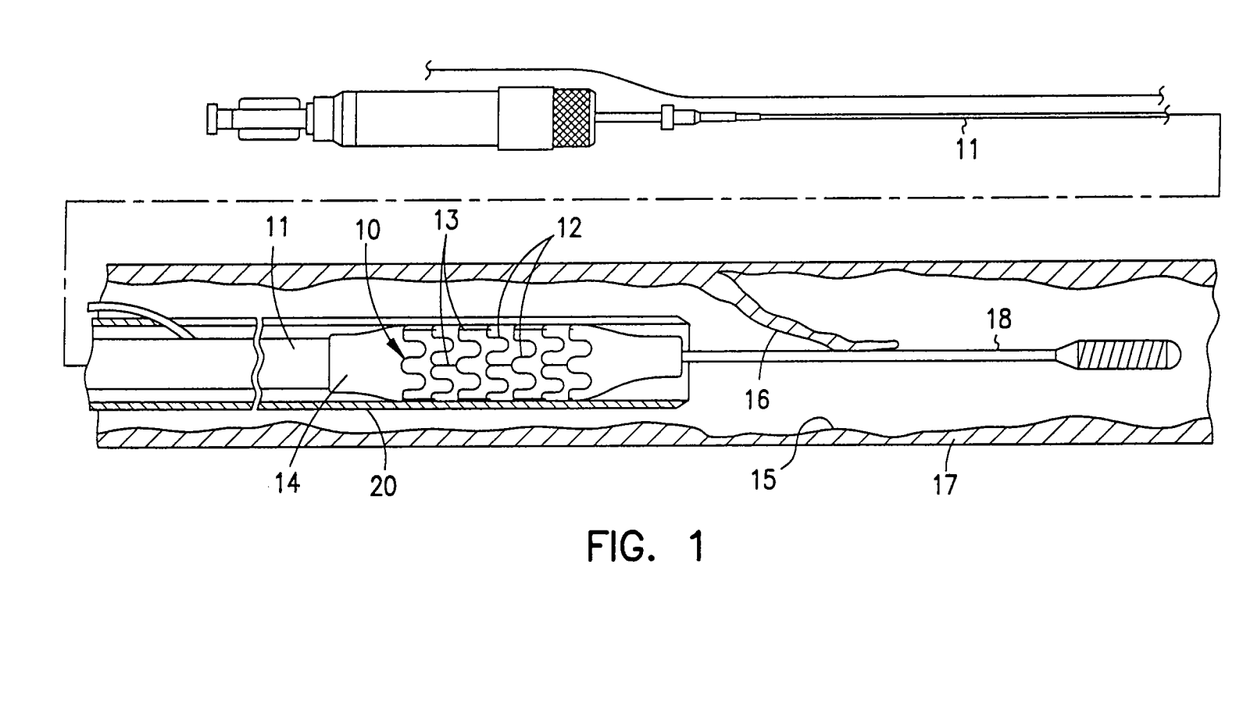
FIG. 1 is an elevational view, partially in section, of one embodiment of a radiopaque stent of the present invention, mounted on a delivery catheter and disposed within a damaged lumen.

The radiopaque stent of the present invention comprises a main body, one embodiment of which is illustrated generally at 10 in FIG. 1, that is fabricated from a cobalt chromium alloy that comprises one or more radiopaque elements. The radiopaque elements are selected from a group of elements with atomic numbers from 40 to 53 that include Zr, Nb, Mo, Tc, Ru, Rh, Pd, Ag, Cd, In, Sn, Sb, Te and I, and those with atomic numbers from 56 to 79 that include Ba, La, Hf, Ta, W, Re, Os, Ir, Pt and Au. These are elements that lie primarily within the transition metal block in the second and third row of the Periodic Table. The cobalt chromium alloy fabricated using these radiopaque elements deforms in a ductile manner, rendering the radiopaque stent of the present invention balloon expandable. A radiopaque cobalt chromium alloy may be applicable to a self-expanding stent.

The term "material" as used herein refers to a substance comprising one or more elements.

For some embodiments, the radiopaque stent of the present invention is fabricated from a single tube subjected to chemical etching, laser machining, conventional machining, electronic discharge machining (EDM), ion milling, slurry jet, or electron beam treatment or combinations of these treatments. For other embodiments, the stent is fabricated from wire elements that are welded together. For additional embodiments, the stent is fabricated from flat stock and is patterned, then rolled and welded. For other embodiments, the stent is fabricated from near-net shape processing such as metal injection molding.

One embodiment of the cobalt chromium alloy-based radiopaque stent of the present invention is comprised of chromium in a concentration of 10-25% by weight, radiopaque elements in a concentration of 10-30% by weight, nickel in a concentration of 5-15% by weight, molybdenum in a concentration of 0-5% by weight, iron in a concentration of 0-5% by weight, manganese in a concentration of 0-5% by weight and other trace materials in a concentration of 1% maximum. The balance of material is cobalt.

The radiopaque stent of the present invention overcomes limitations and weaknesses of other imagable stents by imparting a more visible image when absorbing x-rays during fluoroscopy. With this more visible image, the entire stent is better observed by the interventionalist placing the stent. The image observed by the interventionalist is not "washed out" due to excessive brightness and is not too dim. Because of the improved image, the stent is accurately positioned and manipulated within a lumen of a patient, with a radiopacity such that stent expansion during and after deployment may be assessed accurately by the interventionalist. An additional advantage to the better radiopacity is the visualization of the stent and the underlying vessel during follow-up examinations by the interventionalist.

Because the entire stent is radiopaque, the diameter and length of the stent are readily discerned by the interventionalist. Also, because the stent itself is made of the radiopaque alloy, the stent does not have problems associated with radiopaque coatings, such as cracking or separation or corrosion. Also, because the entire stent is radiopaque, the stent does not require extra markers with their attendant issues.

The low profile of the cobalt chromium stent of the present invention, coupled with its enhanced radiopacity renders the stent more deliverable with easier observation and detection throughout its therapeutic use than stents heretofore available. A stent constructed of a radiopaque cobalt chromium alloy can be made thinner than one of stainless steel without sacrificing fluoroscopic visibility. The low profile of the cobalt chromium stent of the present invention renders the stent more deliverable with greater flexibility.

Furthermore, improved radiopacity of the low profile stent of the present invention increases deliverability of the stent and offers solid performance advantages regarding decreasing the fluid mechanical disturbances of blood flow. Improved radiopacity assists the physician in placing the device precisely. Inflation of the stent is better monitored because the stent is visible to the interventionalist. This visibility reduces the incidence and probability of an underdeployed-stent. Further, in-stent restenosis is monitored as the stent and an injected contrast agent are able to be imaged simultaneously. Unlike some stents, the stent of the present invention does not produce an image which is too bright, thereby obscuring imaging of the underlying vessel morphology.

Many cobalt chromium alloys, although very strong, have an insufficient percent elongation for use in a stent. It has been found that the alloys described herein have at least 20% or greater elongation and thereby should achieve adequate stent-expansion. Some of the cobalt chromium alloys of the present invention also include materials such as tungsten or tantalum. These materials not only impart an optimum radiopacity to the cobalt chromium alloy but also impart corrosion resistance and a resistance to oxidation at high temperatures.

It is believed that a cobalt chromium alloy that contains 15% by weight tungsten is radiopaque to a degree suitable and within the scope of the present invention. The cobalt chromium alloy L-605 has a minimum ultimate tensile strength of 125 ksi, a minimum yield strength of 45 ksi and a minimum total elongation of 30%.

Although the cobalt chromium alloys such as L-605 have not been previously used in the manufacture of stents, the alloy has had use in orthopedic cerclage wires and blood contacting applications in heart valves. In these applications, no problems related to biocompatibility have been found.

The cobalt chromium alloy-based radiopaque stent of the present invention is suitable for use in conjunction with MRI imaging. Many cobalt chromium alloys such as MP35N and L-605 are nonmagnetic.

Figure 7:
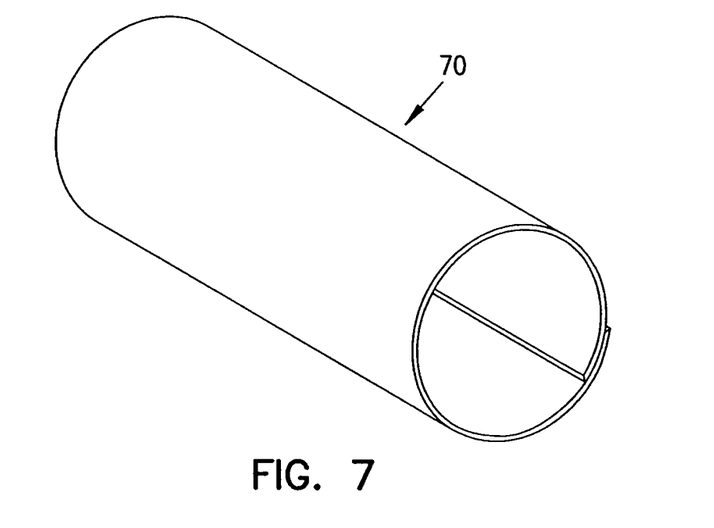
FIG. 7 is a perspective view of one tubular embodiment of the radiopaque stent of the present invention.
Figure 8A:
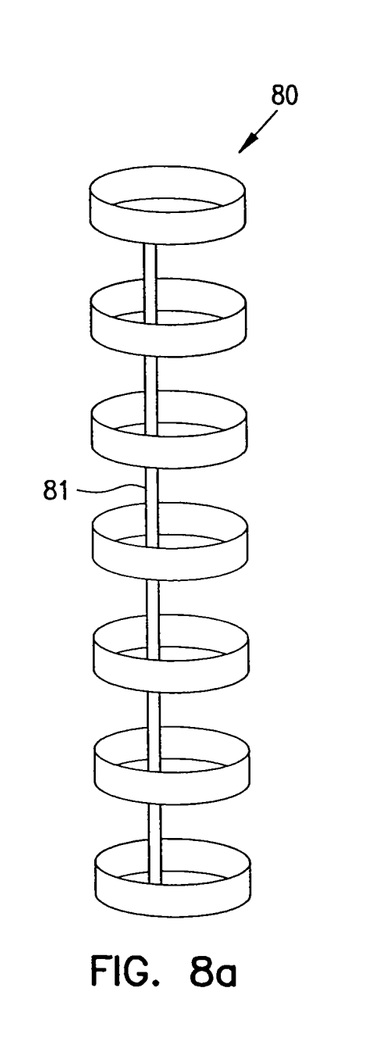
FIG. 8a is a perspective view of one embodiment of the radiopaque stent of the present invention that includes a backbone.
Figure 8B:
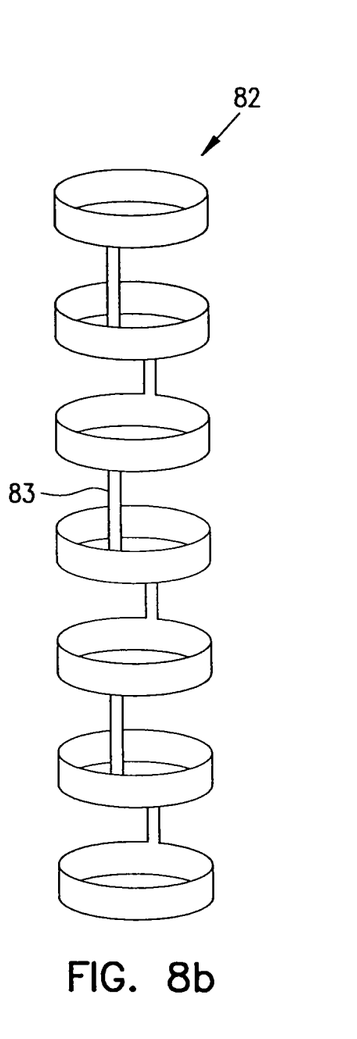
FIG. 8b is a perspective view of one other embodiment of the radiopaque stent of the present invention that includes a staggered backbone.
Figure 9:
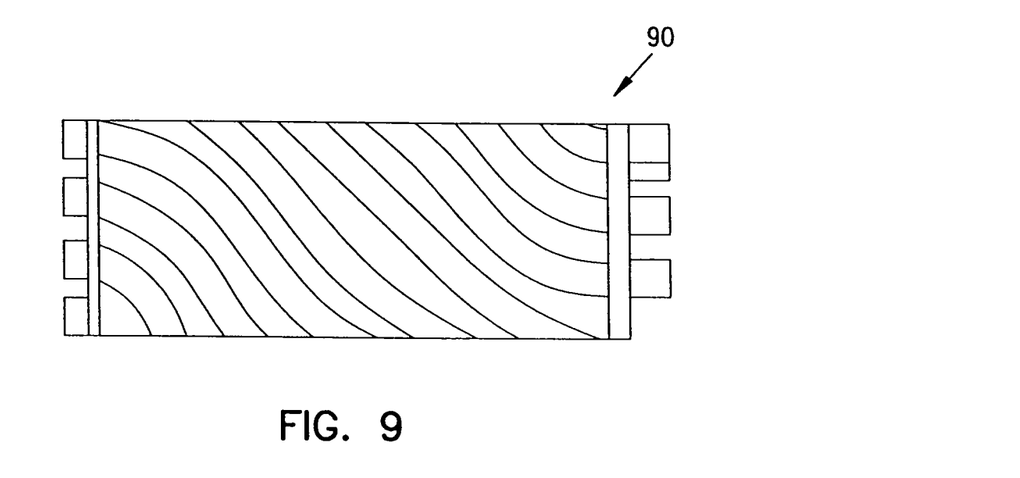
FIG. 9 is a side view of a coiled embodiment of the radiopaque stent of the present invention.
Figure 10:
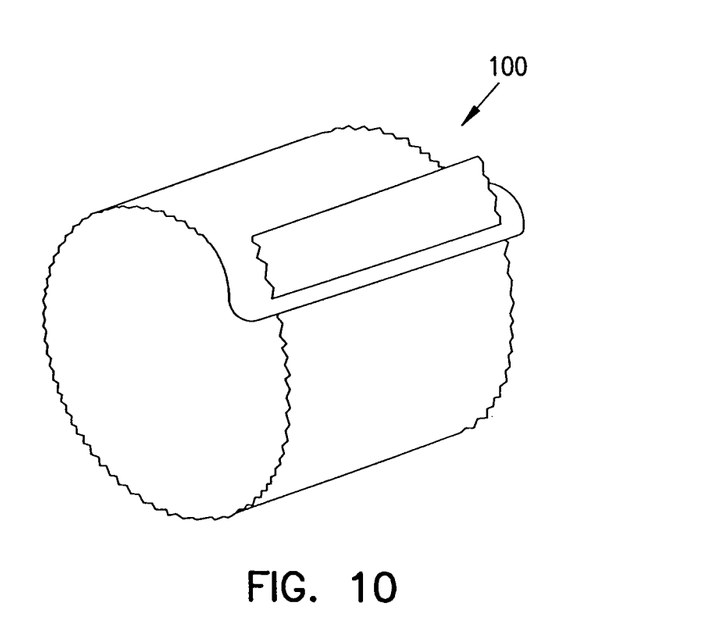
FIG. 10 is a perspective view of a ratcheted embodiment of the radiopaque stent of the present invention.

The radiopaque stent of the present invention is fabricated to have a variety of design embodiments. These design embodiments include a solid cylinder, illustrated at 70 in FIG. 7, a coiled stent illustrated at 90 in FIG. 9, a ratcheting stent 100, illustrated in FIG. 10 and stent embodiment 80 with a backbone 81, illustrated in FIG. 8a and stent embodiment 82 with a staggered backbone, illustrated in FIG. 8b.

One type of radiopaque stent design embodiment is a high precision patterned cylindrical device. This device is illustrated generally at 10 in FIG. 1. The stent 10 typically comprises a plurality of radially expanded cylindrical elements 12 disposed generally coaxially and interconnected by elements 13 disposed between adjacent cylindrical elements.

For some embodiments, the stent 10 is expanded by a delivery catheter 11. The delivery catheter 11 has an expandable portion or a balloon 14 for expanding of the stent 10 within an artery 15. The delivery catheter 11 onto which the stent 10 is mounted is similar to a conventional balloon dilation catheter used for angioplasty procedures. The artery 15, as shown in FIG. 1, has a dissected lining 16 which has occluded a portion of the arterial passageway.

Each radially expandable cylindrical element 12 of the radiopaque stent 10 is independently expandable. Therefore, the balloon 14 may be provided with an inflated shape other than cylindrical, e.g., tapered, to facilitate implantation of the stent 10 in a variety of body lumen shapes.

Figure 2:
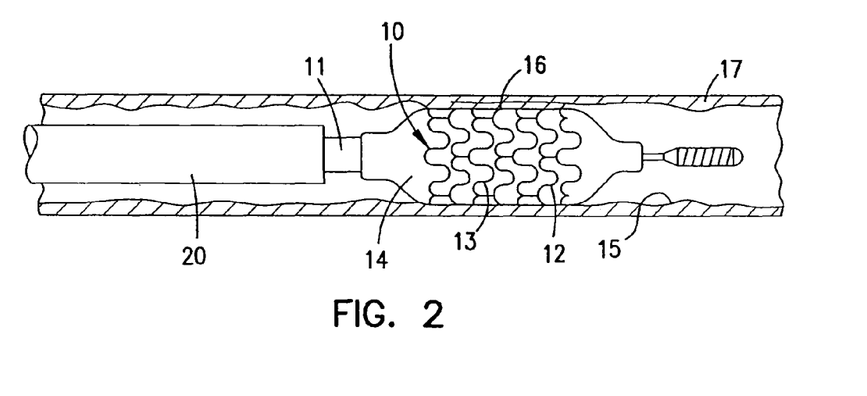
FIG. 2 is an elevational view, partially in section, showing one embodiment of the radiopaque stent of the present invention expanded within a damaged lumen.

The delivery of the radiopaque stent 10 is accomplished by mounting the stent 10 onto the inflatable balloon 14 on the distal extremity of the delivery catheter 11. The catheter-stent assembly is introduced within the patient's vasculature using conventional techniques through a guiding catheter which is not shown. A guidewire 18 is disposed across the damaged arterial section and then the catheter-stent assembly is advanced over a guidewire 18 within the artery 15 until the stent 10 is directly under detached lining 16 of the damaged arterial section. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of a stenotic portion of an artery, the artery may have to be expanded considerably in order to facilitate passage of blood or other fluid therethrough. This expansion is easily observable by the interventionalist with the radiopaque stent of the present invention. While balloon expandable stents are described, it is contemplated that some stent embodiments of the present invention are self expanding.

Figure 3:
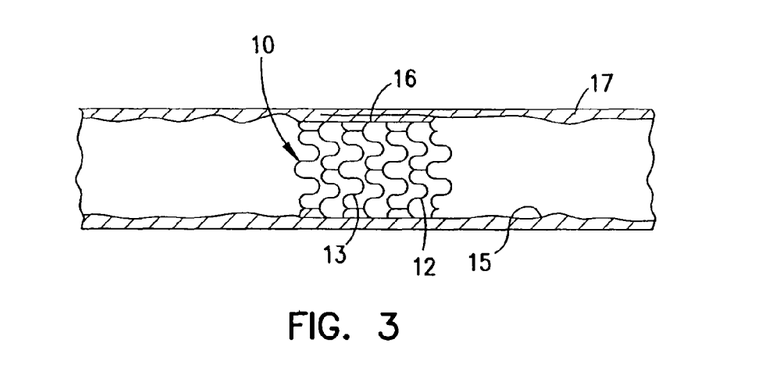
FIG. 3 is an elevational view, partially in section showing the expanded radiopaque stent within the lumen after withdrawal of the delivery catheter.

The stent 10 serves to hold open the artery 15 after the catheter 11 is withdrawn, as illustrated in FIG. 3. Due to the formation of the stent 10 from the elongated tubular member, the undulating component of the cylindrical elements of the stent 10 is relatively flat in transverse cross section so that when the stent is expanded, the cylindrical elements are pressed into the wall of the artery 15 and as a result do not interfere with the blood flow through the artery 15. The cylindrical elements 12 of the stent 10 which are pressed into the wall of the artery 15 are eventually covered with endothelial cell growth which further minimizes blood flow interference. The undulating pattern of the cylindrical sections 12 provides good characteristics to prevent stent movement within the artery. Furthermore, the closely spaced cylindrical elements at regular intervals provide uniform support for the wall of the artery 15, and consequently are well adapted to tack up and hold in place small flaps or dissections in the wall of the artery 15 as illustrated in FIGS. 2 and 3. The undulating pattern of the radiopaque stent is readily discernable to the interventionalist performing the procedure.

Figure 4:
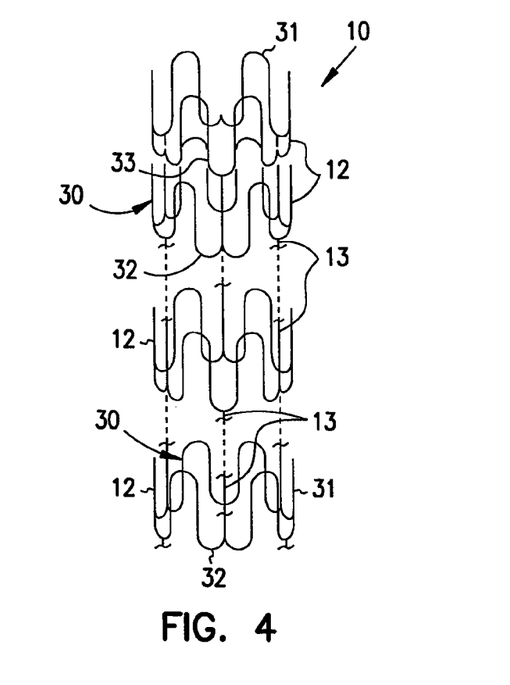
FIG. 4 is a perspective view of one embodiment of the radiopaque stent of the present invention in an unexpanded state, with one end of the stent being shown in an exploded view to illustrate the details thereof.

FIG. 4 is an enlarged perspective view of the stent 10 shown in FIG. 1 with one end of the stent shown in an exploded view to illustrate in greater detail the placement of interconnected elements 13 between adjacent radially expandable cylindrical elements 12. Each pair of interconnecting elements 13 on one side of the cylindrical element 12 are positioned to achieve maximum flexibility for the stent 10. In an embodiment shown in FIG. 4, the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent are secured to either the peaks or valleys of the undulating structural elements in order to prevent shortening of the stent during the expansion thereof.

Figure 5:
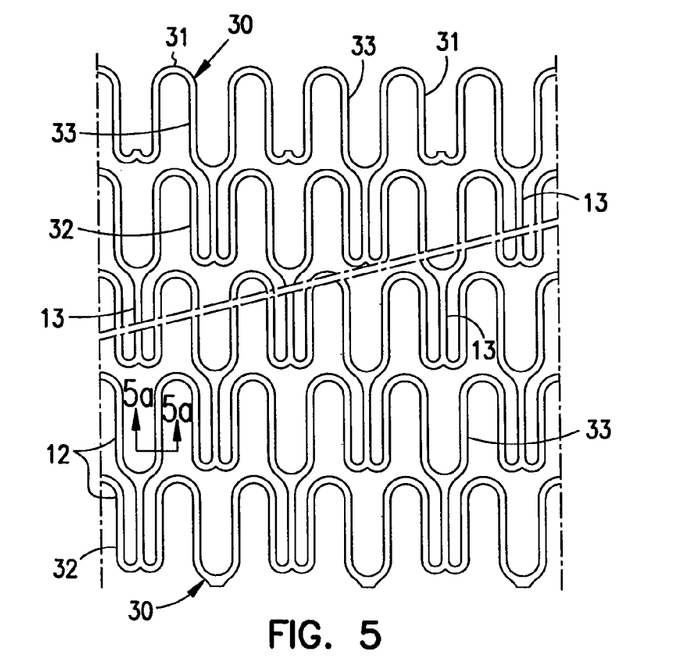
FIG. 5 is a plan view of a flattened section of one radiopaque stent embodiment which illustrates an undulating pattern of the stent shown in FIG. 4.
Figure 5A:
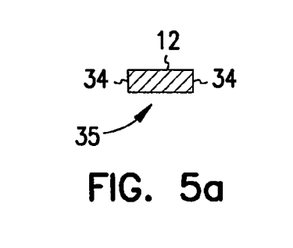
FIG. 5a is a sectional view taken along the line 5a-5a in FIG. 5.

The number of undulations may be varied to accommodate placement of interconnecting elements 13, e.g., at the peaks of the undulations or along the sides of the undulations as shown in FIG. 5.

As best observed in FIGS. 4 and 5, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32 and Y-shaped members 33, each having a different radius so that expansion forces are more evenly distributed over the various embodiments.

The illustrative stent 10 and other stent structures can be made using several techniques, including laser machining. One method of making the radiopaque stent is to cut a thin walled tubular member made of the radiopaque cobalt chromium alloy described herein, to remove portions of the tubing in a desired pattern for the stent, leaving relatively untouched the portions of the radiopaque cobalt chromium tubing which are to form the stent. In accordance with one method of making the device of the present invention, the tubing is cut in a desired pattern using a machine-controlled laser as illustrated schematically in FIG. 6.

The tubing is a cobalt chromium tubing with radiopaque elements. One formulation is L-605, also known as a Haynes 25, MSRR 9500/23. AMS 5796, UNS R30605, 52Co 20Cr 10Ni 15W, OMAT 3/64A, Alacrite X.S.H. The elemental composition of L-605 is as follows:

| Element | Weight Percent |
|---------|----------------|
| Co | balance |
| Cr | 19–21% |
| W | 14–16% |
| Ni | 9–11% |
| Fe | 3% max |
| Mn | 1–2% |
| Si | 0.40% max |
| P | 0.04% max |
| C | 0.05–0.15% |
| S | 0.03% max |

This alloy has a melting range of 2425 to 2570 degrees Fahrenheit, a maximum hardness of 277 HB and a density of 9.1 gm/cc. This alloy in annealed bar form has a minimum ultimate tensile strength of 125 ksi, a minimum yield strength of 45 ksi and a minimum total elongation of 30%.

Other acceptable cobalt chromium alloys have the following elemental composition:

| Element | Weight Percent |
|---------|----------------|
| Co | Balance |
| Cr | 10–25% |
| W and/or Ta | 10–30% |
| Ni | 5–30% |
| Fe | 5% max |
| Mn | 1–5% |
| Mo, Si, P, C, S | 1% max |

Typically, before crimping, the stent has an outer diameter on the order of about 0.04 to 0.10 inches in the unexpanded condition, approximately the same outer diameter of the tubing from which it is made, and may be expanded to an outer diameter in a range of about 1 to 15 millimeters. Stents for peripheral and other larger vessels may be constructed from larger diameter tubing. The strut thickness in a radial direction is in a range of 0.001 to 0.01 inches.

Figure 6:
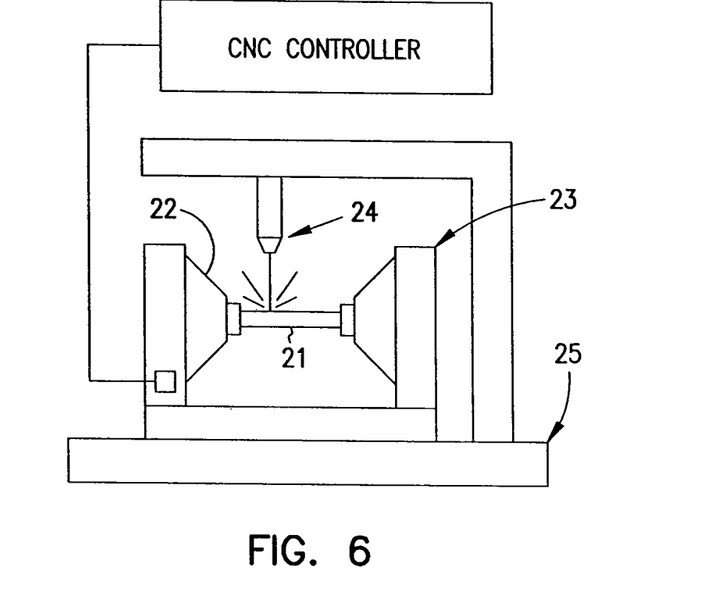
FIG. 6 is a schematic representation of equipment for selectively cutting the tubing in the manufacture of the radiopaque stent of the present invention.

Referring to FIG. 6, in one fabrication embodiment, the tubing 21 is put in a rotatable collet fixture 22, of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the material from the tubing by ablation and a pattern is cut into the tube. The tube is therefore cut into the discrete pattern of the finished stent.

The process for cutting a pattern for the stent into the tubing is automated except for loading and unloading the length of tubing. Referring again to FIG. 6, it may be done, for example, using a CNC opposing collet fixture 22 for axial rotation of the length of tubing. In conjunction with a CNC X-Y table 25 to move the length of tubing axially relatively to a machine-controlled laser as described. The entire space between collets is patterned using a laser setup of the foregoing example. The program for control of the apparatus is dependent on the particular configuration used.

The tubes are made of one of the cobalt chromium alloys described herein that includes radiopaque elements. The radiopaque materials lie primarily within the transition metal block in the second and third row of the Periodic Table. The tubes have an outside diameter of 0.04 inches to 0.10 inches and a wall thickness of 0.001 inches to 0.010 inches. In one embodiment, the tubes are fixtured under a laser and are positioned utilizing a CNC to generate a very intricate and precise pattern. Due to the thin wall and the small geometry of the stent pattern, it is necessary to have very precise control of the laser, its power level, the focus spot size and the precise positioning of the laser cutting path.

One reason to have precise control of the laser operating parameters is to minimize heat input into the stent structure, which prevents thermal distortion, uncontrolled burnout of the metal, and metallurgical damage from excessive heat. With such lasers, it is possible to make a smooth, narrow cut in the cobalt chromium tubes in very fine geometries without damaging the narrow struts that make up the stent structure. The system of the present invention utilizing such lasers and their available parameter adjustments, makes it possible to cut using a narrow beam which minimizes the heat input into the material.

The positioning of the cylindrical radiopaque cobalt chromium structure requires use of precision CNC equipment. In addition, for some embodiments, a rotary mechanism has been provided that allows the computer program to be written as if the pattern were being cut from a flat sheet. This allows both circular and linear interpolation to be utilized in programming.

The optical system which expands the original laser beam delivers the beam through a viewing head and focuses the beam onto the surface of the tube, incorporates a coaxial gas jet and nozzle that helps remove debris from the cut face and cools the region where the beam interacts with the material as the beam cuts and vaporizes the metal. It is also necessary to block the beam as it cuts the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream which surrounds the focus beam and is directed along the beam axes.

The cutting process utilizes an assist gas with the laser beam, resulting in a narrow cut area and minimal molten slag along the cut. In order to remove the slag debris from the cut allowing the scrap to be removed from the remaining stent pattern, it is necessary to soak the cut tube in solutions of mineral acids. Before it is soaked, the tube is ultrasonically cleaned in a mineral acid solution after cutting.

Direct laser cutting produces edges which are essentially perpendicular to the axes of the laser cutting beam in contrast with chemical etching and the like which may produce patterned edges which are angled. Hence, the laser cutting process essentially provides stent cross sections from cut- to- cut which are square or rectangular. As depicted, cylindrical elements 12 are comprised of struts 30 which have generally rectangular cross sections 32 wherein the stent is laser cut from a tubular member. The struts have generally perpendicular edges 31 formed by the laser cut. The resulting stent structure provides superior performance.

In other embodiments, the radiopaque cobalt chromium stent of the present invention is fabricated of radiopaque cobalt chromium alloy wire elements. In another embodiment, the stent is made of a radiopaque cobalt chromium flat stock. In another embodiment, the stent is made of radiopaque cobalt chromium materials using near-net shape processing such as metal injection molding.

When expanded, the stent of the present invention covers about 10-45% of an arterial wall surface area. The radiopaque cobalt chromium stent of the present invention can withstand at least about 30% tensile deformation before failure.

EXAMPLE 1

The alloy used was cobalt chromium L-605 per ASTM specification F90-97. Small diameter tubing was fabricated of fully solution annealed rod stock. After gun-drilling, the resulting tube was cold drawn down in stages. Between draws, the alloy was annealed to maintain ductility. Final dimensions of the tube were about 0.070 inches outer diameter by a 0.004 inch thick wall. The material passed the cytotoxicity and hemolysis test per ISO 10993 indicating a basic level of biocompatibility. A serpentine pattern was cut into the tubing utilizing a laser in a CNC controlled machine as depicted in FIG. 6. After laser cutting, the slag was removed from the stents by a combination of sonication and soaking in a mineral acid solution. Using a 4.0×20 mm ACS ROCKE™ balloon dilatation catheter the stents were expanded to 4.0 mm diameter. Inspection by light microscope and scanning electron microscopy confirmed that there were no cracks or broken struts in the stent indicating the alloy had sufficient ductility to accommodate stent expansion. A comparative radiopacity analysis was done using fluoroscopy. The radiopaque cobalt chrome stent (average thickness 76 microns) was compared to:
1. MULTI-LINK® DUET™, 316L stainless steel, average thickness 140 microns;
2. A 316L stent of the same serpentine pattern as the radiopaque cobalt chrome stent with an average strut thickness of 80 microns.

Visual inspection and computer densitometry analysis of the fluoroscopic images showed the radiopaque cobalt chrome to be more radiopaque than the stainless steel stent of the same design and thickness, as well as the stainless steel DUE™.

EXAMPLE 2

One other alloy suitable for use in the present invention is HAYNES alloy 188, which is a cobalt-nickel-chromium-tungsten alloy. This alloy has good ductility and is readily fabricated by conventional techniques, such as cold working, forging or other hot working methods. This alloy also shows good corrosion resistance to chloride and oxidizing environments. The 188 alloy is produced in the form of plate, sheet, strip, billet, bar, wire, pipe and tubing.

In rod form, the 188 alloy has an ultimate tensile strength of about 137 ksi, a 0.2% yield strength of 67 ksi and an ultimate elongation in 2 inches of 53%. The 188 alloy has a comparative impact strength after 8000-hour exposures of 143 ft.-lbs, solution-annealed Charpy V-Notch Impact test.

While particular forms of the invention have been illustrated and described, various modifications can be made without departing from the spirit and scope of the invention.

What is claimed is:

1. A method for making a radiopaque stent, comprising:
   forming a tube from a cobalt chromium alloy that comprises cobalt, chromium and one or more radiopaque materials, the one or more radiopaque materials being selected from elements with atomic numbers from 56 to 79, the tube having a peripheral exterior surface and an interior surface; and
   shaping the tube to form the radiopaque stent such that substantially the entirety of the stent is fabricated from the cobalt chromium alloy including the one or more radiopaque materials, shaping the tube including removing portions of the tube and leaving relatively untouched portions to form the radiopaque stent, the peripheral exterior surface of the relatively untouched portions forming a stent peripheral exterior surface of the radiopaque stent and the interior surface of the relatively untouched portions forming a stent interior surface of the radiopaque stent, wherein the radiopaque stent exhibits an ultimate elongation greater than about 20%.

2. The method of claim 1, wherein the tube is shaped by cutting or etching.

3. The method of claim 1, wherein the tube is cut by a laser.

4. The method of claim 1, and further comprising cleaning the radiopaque stent.

5. The method of claim 1, and further comprising providing a flat stock comprising the cobalt chromium alloy that comprises the cobalt, the chromium and the one or more radiopaque materials; rolling the flat stock and welding the flat stock to form the tube.

6. The method of claim 1, wherein the tube is shaped by near net shape manufacturing.

7. The method of claim 6, where in the near net shape manufacturing comprises metal injection molding.

8. The method of claim 1, wherein the one or more radiopaque materials comprise tungsten.

9. A method for positioning a stent in a lumen of a living being, comprising:
   providing a radiopaque stent for positioning in a living being, the radiopaque stent having a single cylindrical main body having a peripheral exterior surface and an interior surface, the single cylindrical main body being formed from a processed fully solution annealed rod stock of a cobalt chromium alloy that comprises cobalt, chromium, and one or more radiopaque materials selected from elements with atomic numbers from 56 to 79 and wherein the stent is unexpanded, portions of the processed fully solution annealed rod stock forming the peripheral exterior surface and the interior surface of the single cylindrical main body; wherein the radiopaque stent exhibits an ultimate elongation greater than about 20%
   transporting the radiopaque stent to a lesion site in the lumen wherein the stent is optionally imaged during transport; and
   expanding the radiopaque stent to contact the lesion wherein the stent is imaged during or after expanding the radiopaque stent.

10. A method for making a radiopaque stent, comprising:
    providing one and only one tube comprising a cobalt chromium alloy that comprises cobalt, chromium and one or more radiopaque materials selected from elements with atomic numbers from 56 to 79, the one and only one tube having a peripheral exterior surface and an interior surface; and
    shaping the one and only one tube to form the radiopaque stent, portions of the peripheral exterior surface forming a stent peripheral exterior surface of the radiopaque stent and the interior surface of the portions forming a stent interior surface and forming a longitudinal lumen of the radiopaque stent, wherein the radiopaque stent exhibits an ultimate elongation greater than about 20%.

11. The method of claim 10, wherein the one or more radiopaque materials comprise tungsten.

12. The method of claim 10, further comprising cold drawing the one and only one tube in stages.

13. The method of claim 10, wherein the one and only one tube is shaped by cutting or etching.

14. The method of claim 10, wherein the one and only one tube is cut by a laser.

15. The method of claim 10, further comprising cleaning the radiopaque stent.

16. The method of claim 10, further comprising forming the one and only one tube from an annealed rod stock.

17. The method of claim 16, wherein the annealed rod stock is fully solution annealed.

18. The method of claim 17, further comprising gun-drilling the fully solution annealed rod stock.

* * * * *